United States Patent [19]

Bergstrom et al.

[11] 4,247,544
[45] Jan. 27, 1981

[54] C-5 SUBSTITUTED URACIL NUCLEOSIDES

[75] Inventors: Donald E. Bergstrom, Davis; Jerry L. Ruth, Encinitas, both of Calif.

[73] Assignee: The Regents of the University of California, Berkeley, Calif.

[21] Appl. No.: 53,925

[22] Filed: Jul. 2, 1979

[51] Int. Cl.³ .................... A61K 31/70; C07H 17/00
[52] U.S. Cl. ................................. 424/180; 536/23
[58] Field of Search ....................... 536/23; 424/180

[56] References Cited

U.S. PATENT DOCUMENTS 3,282,921  11/1966  Verheyden et al. ................ 536/23

OTHER PUBLICATIONS

Montgomery et al., J. Heterocycl. Chem., 2, 313 (1965).
Bergstrom, et al., J. Am. Chem. Soc., 98, 1587 (1976).
Kulikowski et al., J. Med. Chem., 17, 269 (1974).

Primary Examiner—Johnnie R. Brown
Assistant Examiner—Blondel Hazel
Attorney, Agent, or Firm—Bertram I. Rowland

[57] ABSTRACT

Compounds of the formula

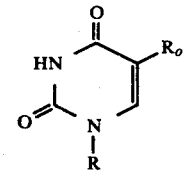

wherein $R_o$ is —CH=CH—CH$_3$ or —CH=CH—CF$_3$ and R is β-D-ribofuranosyl, β-D-2-deoxyribofuranosyl or β-D-arabinofuranosyl are useful as antiviral agents.

7 Claims, No Drawings

C-5 SUBSTITUTED URACIL NUCLEOSIDES

The invention described herein was made in the course of, or under, a grant from the National Cancer Institute.

The present invention relates to the chemistry of nucleosides and, more particularly, is directed to novel C-5 substituted uracil nucleosides and the use of such compounds as antiviral agents.

The subject compounds of the present invention can be represented by the following generic formula:

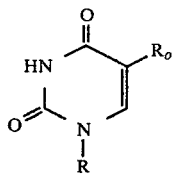

wherein $R_o$ is —CH=CH—CH$_3$ or —CH=CH—CF$_3$ and R is β-D-ribofuranosyl, β-D-2-deoxyribofuranosyl or β-D-arabinofuranosyl.

Compounds embraced by generic formula (I) can be represented subgenerically as

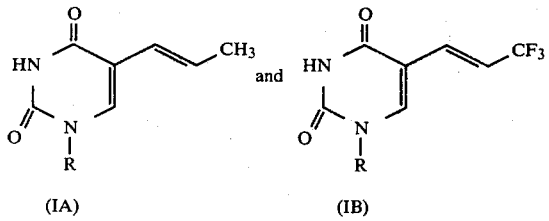

where R is as previously defined.

Preferred compounds embraced by subgeneric formulas (IA) and (IB) are those wherein R is β-D-2-deoxyribosyl or β-D-arabinofuranosyl.

Particularly preferred compounds within the group described in the previous paragraph are compounds of formula (IB).

The subject compounds of formula (I) are particularly useful as antiviral agents in treatment of numerous mammalian viral infections such as herpes simplex type 1 and type 2, vaccinia, cytomegalovirus and the like. In addition, the subject compounds are useful as antineoplastic agents and also produce metabolic deficiencies in biological systems such as in vitro and in vivo inhibition of enzymes requisite for DNA and/or RNA synthesis, or are precursors for compounds which produce such deficiencies.

Accordingly, a further aspect of the present invention relates to pharmaceutical compositions which comprise the subject compounds of formula (I) in combination with a pharmaceutically acceptable non-toxic carrier.

Useful pharmaceutical carriers for the preparation of the compositions hereof can be solids, liquids, or gases. Thus, the compositions can take the form of tablets, pills, capsules, powders, sustained release formulations, solutions, suspensions, elixirs, aerosols, and the like. The carriers can be selected from the various oils including those of petroleum, animal, vegetable or synthetic origin. Specific oils that may be employed include peanut oil, soybean oil, mineral oil, sesame oil and the like. Water, saline, aqueous dextrose and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, and the like. Suitable pharmaceutical carriers and their formulation are described in "Remingtons Pharmaceutical Sciences" by E. W. Martin. Such compositions will, in any event, contain an effective amount of the active compound together with a suitable amount of carrier so as to prepare the correct dosage form for proper administration to the host.

The present invention also relates to a method of treating a virus infection in a host subject afflicted with same, which method comprises administering to the host subject an effective amount of a compound of the present invention or a suitable composition containing same.

In general, it is expedient to administer the subject compounds in amounts of between about 1 and 100 mg/kg body weight per day or other regular course of treatment (preferably between 5 and 50 mg/kg body weight per day) distributed in several individual doses in order to achieve effective results. The subject compounds and compositions may be administered by conventional methods, e.g., typically, orally, parenterally and the like, and in any form suitable for the administration mode, i.e., isotonic solutions, suspensions, tablets, capsules and the like.

The exact dosage and regimen for administration of the compounds and compositions disclosed herein will necessarily be dependent upon the needs of the host subject being treated, the type of virus involved and the compound employed. In any event the compositions to be administered will contain a quantity of the subject compound in an amount effective for relief of the specific condition being treated.

In addition to manifesting a high order of activity against various viruses, the compounds of the present invention are relatively non-cytotoxic. For example, when tested against a prototype strain (HSV-1), the therapeutic index is usually greater than 1000. Comparable compounds which have been suggested as antiviral agents do not combine this high order of activity with low toxicity (e.g., compounds such as 5-ethynl-2'-deoxyuridine have a therapeutic index in HSV-1 approaching 10).

Standard testing procedures include use of common cell lines such as HeLa, rabbit kidney, mouse embryo, human skin fibroblast and the like. For testing, confluent cell monolayers are infected with virus (usually 10 plaque-forming units per cell), allowed to absorb for 1 hour at 37° C., and then washed. A solution of known concentration of test compound in Eagle's essential medium containing 10% calf serum is added to the monolayer in appropriate volumes. The monolayer is then incubated at 37° C. for 30–48 hours and then frozen at −70° C. until titration. In each experiment, toxicity controls (omitting virus), virus controls (omitting test compound), and cell controls (omitting both test compound and virus) are run simultaneously.

DETAILED DESCRIPTION

The present invention, in a still further aspect, is directed to methods for the preparation of the subject compounds, which methods can be schematically represented as follows:

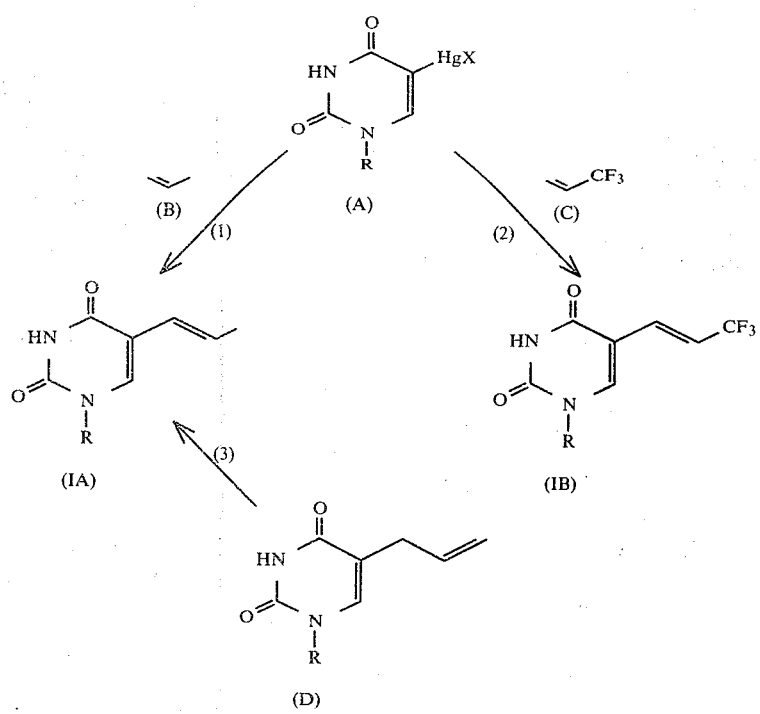

wherein X is a conventional ligand such as chloro, acetoxy or trifluoroacetoxy; and R is β-D-ribofuranosyl, β-D-2-deoxyribofuranosyl or β-D-arabinofuranosyl.

Reaction (1) in the above schematic diagram can be conveniently effected by treating a C-5 mercurated uracil nucleoside (A) with propane (B) in the presence of an inorganic or organic palladium (II) complex using one to three atmospheres of (B), and employing the palladium complex (1) in slight molar excess of (A), i.e. 1.1 to 2.5 equivalents, or (2) in catalytic amounts, i.e., 0.01 to 0.5 equivalents, if a suitable reoxidant such as, for example, copper (II) chloride is included. The reaction is carried out in a suitable solvent at temperatures in the range of 0° C. to 60° C., preferably at about room temperature, for about from 1 to 24 hours, preferably about 2 hours. Suitable solvents include, for example, methanol, isopropanol, N,N-dimethylformamide, acetonitrile, methyl formate, water and the like, and mixtures thereof. Suitable palladium complexes that may be employed include, for example, lithium tetrachloropalladate ($Li_2PdCl_4$) and lithium trichloropalladate ($LiPdCl_3$) as well as other alkaline or alkaline earth metal palladates; palladium (II) chloride, palladium (II) acetate and other complexes of palladium (II) with conventional ligands. The preferred palladium complex is $Li_2PdCl_4$.

Reaction (2) can be effected by treating a C-5 mercurated uracil nucleoside (A) with 3,3,3-trifluoropropene (C) in the presence of a palladium (II) complex in the manner previously set forth in the description of Reaction (1).

Reaction (3), isomerization of 5-(prop-2-en-1-yl)-uracil nucleoside (D) to a 5-(propen-1-yl)-uracil nucleoside, (IA), is effected in the presence of a rhodium catalyst, such as, for example, $Rh(Ph_3P)_3Cl$, and a suitable solvent. The reaction is typically conducted in 95% ethanol at elevated temperatures, preferably reflux.

The starting materials of formula (A) are known compounds and can be prepared by procedures described by Bergstrom et al in *J. Carbohydrates. Nucleosides. Nucleotides*, 4 (5), 257–269 (1977) and references incorporated therein or by obvious modification of such procedures. The starting materials of formula (D) are also known compounds and can be prepared by procedures described by Ruth et al in *J. Organic Chemistry*, 43, 2870 (1978) and references incorporated therein or by obvious modification of such procedures.

The compounds embraced by formula (IB) may be readily transformed into compounds containing other functional groups. For example, treatment of compounds of formula (IB) with aqueous hydroxide solution effects hydrolysis of the carbon-fluorine bonds to produce the 5-(2-carboxyethen-1-yl)uracil nucleosides.

Separation and isolation of the subject compounds can be effected by any suitable purification procedure such as, for example, evaporation, filtration, crystallization, column chromatography, thin layer chromatography, etc. Specific illustrations of typical separation and isolation procedures can be had by reference to the appropriate examples described hereinbelow; however, other equivalent separation procedures can, of course, also be used. Also, it should be appreciated that where typical reaction conditions (e.g. temperatures, mole ratios, reaction times) have been given that conditions both above and below these ranges can also be used, though generally less conveniently.

The numbering system and nomenclature used to define and describe the subject compounds of the present invention are those conentionally employed in the art. For example, the numbering system for uracil nucleosides is denoted thus:

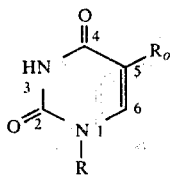

The numbering of carbon atoms in the carbon skeleton of the $R_o$ substituent is such that the carbon atom attached to the uracil ring at position C-5 is designated as 1. This point of attachment of the uracil ring to the C-5 substituent ($R_o$) is designated in the nomenclature employed herein by prefacing "yl" by the number of the "attaching" carbon atom (i.e., 1). For example, 5-(3,3,3-trifluoropropen-1-yl)-1-β-D-arabinofuranosyluracil is structurally denoted as follows:

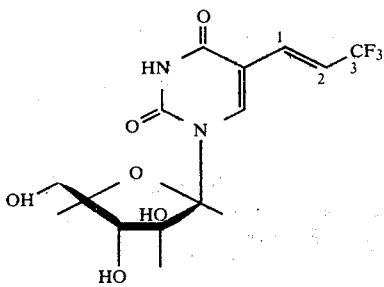

A further understanding of the present invention can be had from the following non-limiting preparations and examples wherein: (1) proton magnetic resonance spectra ($^1$H NMR) are determined at 60 to 100 mHz, the signals are defined as singlet (s), doublet (d), triplet (t), multiplet (m), combinations of these (e.g., dd is doublet of doublets), and descriptive terms such as broad or narrow (locations of absorptions are in ppm downfield from currently employed standards); (2) ultraviolet spectra (UV) are determined, the wavelengths of maximum absorption ($\lambda_{max}^{H2O}$) and of minimum absorption ($\lambda_{min}^{H2O}$) are given in nanometers (nm) for neutral aqueous solutions of the compound; and (3) elemental analyses are determined, the empirical formula of the compound is given with the calculated mass ratios as % of total (e.g., C, 50.88 indicates a calculated 50.88% carbon by weight) and the experimental % by mass are included in like form.

DESCRIPTIONS OF SPECIFIC EMBODIMENTS

The following specific description is given to enable those skilled in the art to more clearly understand and practice the present invention. It should not be considered as a limitation upon the scope of the invention but merely as being illustrative and representative thereof.

EXAMPLE I 5-(Propen-1-yl)-2'-deoxyuridine

A solution of 5-chloromercuri-2'-deoxyuridine (1.1 g, 2.3 mmol) in 25 ml 0.10 N Li$_2$PdCl$_4$ in methanol (2.5 mmol, 1.1 eq) is stirred at room temperature under about 2.5 atmospheres of propylene. After approximately 2 hours, the solution is filtered to remove Pd metal, the filtrate treated with hydrogen sulfide for about one minute, and the insoluble metal sulfides removed by filtration. The methanolic filtrate is concentrated and then column chromatogrammed, first on silica gel eluting with chloroform/methanol gradient, then molecular exclusion resin (such as Bio-Gel P-2) eluting with water. The appropriate fractions are combined, and lyophilized to afford a white solid. Recrystallization from water gives 5-(propen-1-yl)-2'-deoxyuridine as white crystals; m.p. 178°–178.5° C.; $^1$H NMR (D$_2$O)δ 7.8 (s,1H), 6.2 (t,1H, J=6 Hz), 6.1 (m,1H), 6.0 (m,1H), 4.5 (m,1H), 4.5 (m,1H), 4.1 (m,1H), 3.8 (narrow m, 2H), 2.4 (dd, 2H), 1.8 (d,3H); UV $\epsilon_{max}$ 237 nm ($\epsilon$12500), 293 nm ($\epsilon$8000), $\lambda_{min}$ 267 nm (4400). Analysis calculated for C$_{12}$H$_{16}$N$_2$O$_5$, C,53.73; H,6.01; N,10.44; found C,53.88; H,5.95; N,10.67.

5-(Propen-1-yl)-2'-deoxyuridine is also produced by isomerization of 5-(prop-2-en-1-yl)-2'-deoxyuridine with 5 mole % Rh (Ph$_3$P)$_3$Cl in refluxing 95% ethanol followed by column chromatography on molecular exclusion resin as described above.

EXAMPLE II

Repeating the procedure of Example I, but replacing 5-chloromercuri-2'-deoxyuridine with 5-chloromercuriuridine and then with 5-chloromercuri-1-β-D-arabinofuranosyluracil is productive of 5-(propen-1-yl)uridine and 5-(propen-1-yl)-1-β-D-arabinofuranosyluracil, respectively.

EXAMPLE III 5-(3,3,3-Trifluoropropen-1-yl)-2'-deoxyuridine

A solution of 5-chloromercuri-2'-deoxyuridine (2.64 mmol) and Li$_2$PdCl$_4$ (2.9 mmol) in 30 ml methanol is stirred under about 2 atmospheres of 3,3,3-trifluoropropene for about 4 hours at room temperature. The mixture is then filtered, the filtrate treated with hydrogen sulfide for about one minute, and the insoluble metal sulfides removed by filtration. Concentration of the methanolic filtrate followed by column chromatography, first on silica gel eluting with chloroform/methanol gradient and then on molecular exclusion resin eluting with water affords 5-(3,3,3-trifluoropropen-1-yl)-2'-deoxyuridine which is recrystallized from water to give white crystals which decompose upon heating above 140° C.; $^1$H NMR (D$_2$O) δ 8.26 (s,1H), 6.78 (narrow m, 2H), 6.23 (t,1H, J=6.5 Hz), 4.45 (m,1H), 4.0 (m,1H), 3.82 (narrow m,2H), 2.37 (dd,2H); UV $\lambda_{max}$ 285 nm ($\epsilon$6500), 243 nm ($\epsilon$7000), $\lambda_{min}$ 263, 221 nm. Analysis calculated for C$_{12}$H$_{13}$F$_3$N$_2$O$_5$, C,44.72, H,4.07, N,8.69; found C,44.91, H,4.05, N,8.83.

EXAMPLE IV

Repeating the procedure of Example III, but replacing 5-chloromercuri-2'-deoxyuridine with 5-chloromercuriuridine and then with 5-chloromercuri-1-β-D-arabinofuranosyluracil is productive of 5-(3,3,3-trifluoropropen-1-yl)uridine and 5-(3,3,3-trifluoropropen-1-yl)-1-β-D-arabinofuranosyluracil, respectively.

What is claimed is:

1. A compound of the formula:

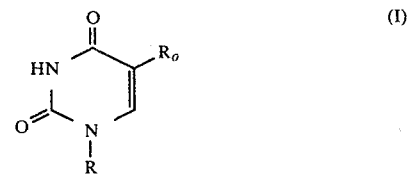

wherein $R_o$ is —CH=CH—CH$_3$ or —CH=CH—CF$_3$ and R is β-D-ribofuranosyl, β-D-2-deoxyribofuranosyl or β-D-arabinofuranosyl.

2. A compound according to claim 1 wherein R is β-D-2-deoxyribofuranosyl or β-D-arabinofuranosyl.

3. A compound according to claim 2 wherein $R_o$ is —CH=CH—CF$_3$.

4. The compound according to claim 3 which is 5-(3,3,3-trifluoropropen-1-yl)-2'-deoxyuridine.

5. The compound according to claim 3 which is 5-(3,3,3-trifluoropropen-1-yl)-1-β-D-arabinofuranosyluracil.

6. A composition useful for treating HSV-1 virus infections in mammals which comprises an effective amount of compound of the formula

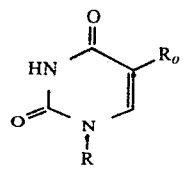

wherein $R_o$ is CH=CH—CH$_3$ or —CH=CH—CF$_3$ and R is β-D-ribofuranosyl, β-D-2-deoxyribofuranosyl or β-D-arabinofuranosyl.

7. A method of treating a HSV-1 virus infection in a host mammal afflicted with such infection which comprises administering to said host an effective amount of the compound of the formula

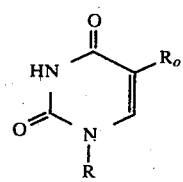

wherein $R_o$ is —CH=CH—CH$_3$ or —CH=CH—CF$_3$ and R is β-D-ribofuranosyl, β-D-2-deoxyribofuranosyl or β-D-arabinofuranosyl.

* * * * *